United States Patent [19]

Bendel et al.

[11] Patent Number: 4,905,695
[45] Date of Patent: Mar. 6, 1990

[54] STERILE SURGICAL NEEDLE HAVING DARK NON-REFLECTIVE SURFACE

[75] Inventors: Lee Bendel, Lebanon; Florence Stoffel, Ringoes, both of N.J.

[73] Assignee: Ethicon, Inc., Somerville, N.J.

[21] Appl. No.: 160,226

[22] Filed: Feb. 25, 1988

Related U.S. Application Data

[63] Continuation-in-part of Ser. No. 926,759, Nov. 4, 1986, abandoned, which is a continuation-in-part of Ser. No. 632,343, Jul. 19, 1984, abandoned.

[51] Int. Cl.⁴ .................................. A61B 17/06
[52] U.S. Cl. ............................. 606/222; 148/242
[58] Field of Search .............. 128/339, 337; 148/6.11, 148/6.14 R

[56] References Cited

U.S. PATENT DOCUMENTS

| | | | |
|---|---|---|---|
| 2,537,035 | 1/1951 | Clingan | 148/6.11 |
| 2,865,376 | 12/1958 | Pellier et al. | 128/339 |
| 3,038,475 | 6/1962 | Orcutt | 128/339 |
| 3,142,592 | 7/1964 | Certa et al. | 148/6.14 R |
| 4,660,559 | 4/1987 | McGregor et al. | 128/339 |
| 4,726,368 | 2/1988 | Morris | 128/339 |

FOREIGN PATENT DOCUMENTS 0168833  1/1986  European Pat. Off. ............ 128/339

OTHER PUBLICATIONS

Surgical Needle Brochure, "VISI—BLACK" surgical needle, Ethicon, Inc., Copyright 1984.

Primary Examiner—Edward M. Coven
Assistant Examiner—Gary Jackson
Attorney, Agent, or Firm—Robert L. Minier

[57] ABSTRACT

A sterile surgical needle having a dark, non-reflective and non-flaking surface. The needle is produced by selecting an appropriately shaped needle having the desired degree of sharpness. The needle is treated to activate the surface and then immersed in a solution of sulfuric acid, potassium dichromate and water to form a dark, non-reflective, non-flaking surface. The needle is sterilized to produce a sterile surgical needle of improved visibility.

1 Claim, 1 Drawing Sheet

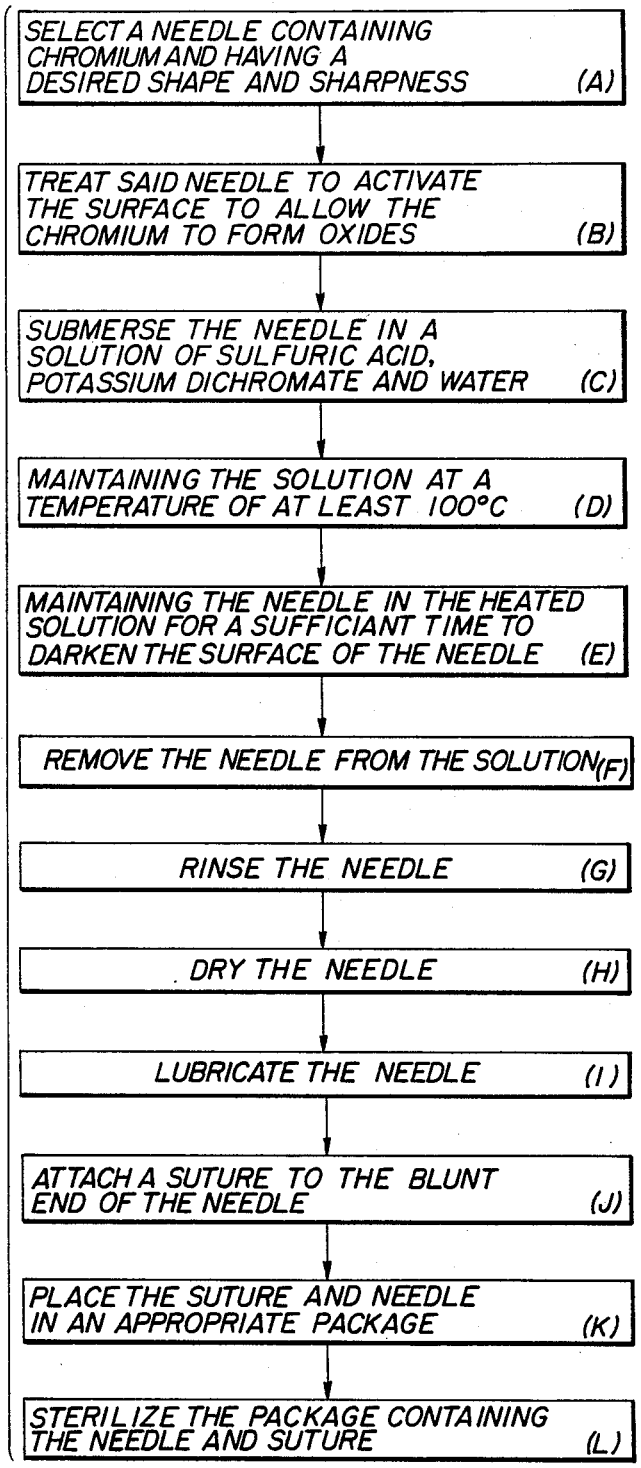
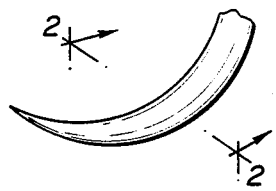

STERILE SURGICAL NEEDLE HAVING DARK NON-REFLECTIVE SURFACE

RELATED APPLICATIONS

This patent application is a continuation-in-part application of co-pending application Ser. No. 926,759, filed Nov. 4, 1986, which was a continuation-in-part application of Ser. No. 632,343, filed July 19, 1984 both now abandoned.

The present invention relates to sterile surgical needles, and more particularly to such needles which have a uniformly dark and non-reflective surface.

BACKGROUND OF THE INVENTION

In the past, sterile surgical needles generally have had a bright or shiny chromium or silver type of surface. It was thought this shiny surface, which was a result of polishing for the most part, was required in order to obtain desired sharpness and cutting characteristics or penetration characteristics with the needle. A drawback to these shiny surfaces is the difficulty they present in being observed by the surgeon during a surgical procedure. Cardiovascular surgeons and micro-surgeons have found it quite difficult to use needles which reflect light in surgery because of the reduced visibility of such needles. With the advent of micro-surgery there is a similar problem in lack of visibility within the surgical site of these highly reflective needles.

Methods of blackening the reflective surfaces of metal materials have been known for sometime and have been attempted with surgical needles. To the best of my knowledge, no one has been able to develop a suitably dark, non-reflective needle as these blackening processes suffer from one or more disadvantages. Often these blackening processes form a coating on the needle which may flake off during use. In some instances the processes form a non-uniform non-reflective surface which causes visibility problems as well as interfering with the sharpness characteristics of the needle. In most of these blackening Processes the needle becomes dull as a result of the blackening treatment.

What I have discovered is a new method for blackening surgical needles and a new method for producing sterile surgical needles having a dark and non-reflective surface. The surface of my new needles doos not flake and my new needles have excellent sharpness and penetration characteristics. Other objects and advantages of the present invention will become readily apparent from a reading of the following detailed description and drawings.

SUMMARY OF THE PRESENT INVENTION

In accordance with the present invention, my new sterile surgical needle has a uniformly dark and non-reflective surface. The surface is non-flaking and the needle has Penetration characteristics substantially the same as needles having shiny and polished surfaces. The preferred needles of the present invention have a matte black surface. The method of the Present invention for producing my new needles is to first select a needle containing chromium. The needle should have the desired shape or configuration and degree of sharpness. The surface of the selected needle is treated by electrical processes to activate the surface by eliminating chromium rich oxides. The treated needle is submersed in a solution of sulfuric acid, potassium dichromate, and water at a temperature in excess of 100° C. The needle is maintained in the bath for a sufficient period of time to uniformly darken the bath for a sufficient period of time to uniformly darken the surface of the needle and render that surface non-reflective. The needle is removed from the bath and may be rinsed with running hot water, ultrasonically rinsed at room temperature, air dried, lubricated and oven dried. It is preferred that the needles be lubricated with silicone and dried. The needle is sterilized by various well known sterilization techniques such as gas sterilization, irradiation, or the like. In most instances, a suture will be attached to the blunt end of the needle and the needle placed in a suitable Package prior to sterilization.

BRIEF DESCRIPTION OF THE DRAWINGS

FIG. 1 is a perspective view of one shape of needle of the present invention;

FIG. 2 is a cross-sectional view taken along line 2—2 of FIG. 1; and

FIG. 3 is a box flow sheet showing the various steps in the method of the present invention

DETAILED DESCRIPTION OF THE INVENTION

Referring to the drawings, in FIG. 1 there is shown one shape of needle of the present invention. In this figure there is shown a curved needle. As shown in FIG. 2 the cross-sectional shape of the needle, at least of the pointed end, is circular. The blunt end of the needle may have a suture attached thereto and in many instances the sides of the needle will be flattened to assist in grasping of the needle b a suitable needle holding instrument. The entire surface of the needle is dark and non-reflective and the surface is uniformly dark and non-reflective. The surface is also non-flaking and the needle has excellent penetration characteristics. In the preferred embodiments of the needles of the present invention, the needle has a matte black finish. The needles of the present invention may be made from any of the various steels containing chromium. The preferred materials are 300 or 400 series stainless steels.

To determine the characteristics of the needle surface, the needles are tested for flaking characteristics. The tenacity and the non-flaking characteristics of the surface are evaluated by grasping the needle with a serrated jawed needle holder such as a Codman Classic Plus needle holder. The needle holder is closed to the first locking position and released. The needle is examined under a scanning electron microscope at a magnification of approximately 500 times to determine whether any of the material has flaked. Also, the needles are examined at a magnification of 20 times to determine the intensity of the color, the edge quality and the uniformity of the colored needle. The blackened needles are passed through a chamois under a microscope to see if any of the surface of the coating comes off on the chamois. The penetration performance of the needle is determined utilizing a curved needle penetration tester. Two sensations are determined when testing the needle for penetration. The first is, the force to initially penetrate the point through a standard material and the second is to determine the drag on a needle as it passes through the appropriate material. The combination of these forces is reflected in the total force to penetrate and is measured on an Instron tester.

FIG. 3 is a block flow diagram depicting the various steps which may be used to produce the needles of the present invention. First and as shown in Box A, the needle having the desired shape and a desired degree of sharpness and made from a steel containing chromium is selected. Steel containing chromiums are required in order to produce hard needles which will retain sharp cutting edges. The selected needle is treated (Box B) to render the surface of the needle activated; that is, to allow the chromium on the surface of the needle to form oxides. Two techniques for activating the surface of the needle are to either electroclean or electropolish the needle immediately before the blackening treatment. If the surface of the needle is not suitably activated, a thin layer of the metal is removed in the process and the cutting edges dulled and the surface roughened or channeled. The dulling and roughening greatly increases the penetration forces required with the needle and make the needle unsuitable for use in many surgical procedures where tissue trauma must be kept to a minimum. The treated needle is submersed in a solution of sulfuric acid, potassium dichromate, and water (Box C). Solutions, having a specific gravity of about 1.5 to 1.6 have been found satisfactory. The solutions are prepared by mixing about 60 to about 65 percent by weight of sulfuric acid with the remainder water. About 7 to about 10 percent of weight of Potassium dichromate is combined with the sulfuric acid water mixture to form the blackening solution. The solution is heated to a temperature of at least 100° C. and maintained at about 100° and below the boiling point of the solution or about 135° C. (Box D). To obtain the advantages of the present invention, it is important that the blackening treatment be carried out at temperatures in excess of 100° C. The needle is maintained in the solution for a sufficient length of time to darken the needle surface (Box E). Periods of time of from about 4 minutes up to 30 minutes or even longer have been found satisfactory. Other dichromate salts, such as sodium dichromate, may also be used.

The needle is removed from the solution (Box F) and the needle rinsed to remove solution residue by running hot water over the needle (Box G). The needle is preferably ultrasonically rinsed needle is lubricated (Box I) and an appropriate suture is attached to the blunt end of the needle (Box J). The blunt end of the needle would usually have a drilled hole or a channel with a suture swaged into the hole or channel as is well known in the art. The needle and suture is packaged in a suitable Package (Box K) and the package sterilized (Box L) by cobalt radiation or ethylene oxide or other sterilization techniques as are well known in the art.

The invention will be more fully described by the following specific examples.

EXAMPLE I

A solution is prepared utilizing 180 mililiters of sulfuric acid, 50 grams of potassium dichromate and 200 mililiters of water. The solution has a specific gravity of from 1.52 to 1.55 and is maintained at a temperature of about 120° to 130° C. A curved needle having a round cross section and made from 45500 stainless steel is electropolished by immersing the needle in a suitable polishing acid and passing a current through the needle using the needle as an anode for from 4 to 60 seconds or more. The polished needle is immersed in the solution for from about 4 to 15 minutes. The needle is removed from the hot solution and rinsed ultrasonically with water. The needle is air dried, lubricated, oven dried and the dry needle examined and tested. The needle is examined under a scanning electron microscope by grasping the needle with a serrated jawed needle holder. The needle has a good matte black surface which is non-reflective and when examined under the electron scanning microscope no flaking of the black surface is detected.

The needle is tested for penetration characteristics by placing the needle in a rotating arm and pushing the needle through the the needle in a rotating arm and pushing the needle through the penetration media following the arc of the needle. A load cell measures the force on the penetration media as the needle passes through. The data is recorded on an X-Y recorder. The needle is 10 mils in diameter and the penetration results are for initial penetration a force of 40 grams and for the drag on the needle as it passes through the media is 18 grams. Similar needles are treated in the same bath. Needles are treated maintaining the bath at a temperature of 120° C. Needles which have had their surfaces treated with electropolishing and untreated needles are placed in the bath for from 5 to 30 minutes. In some cases, the needle has some blackening on the surface but it is not uniform and in other cases the black surface which, though it may be uniform, is shiny and reflective.

EXAMPLE III

A needle which has not been treated to activate the surface is placed in the bath described in Example I while the bath is maintained at a temperature of 120° to 130° C. The needle is maintained in the bath for about 15 minutes. The resulting needle has a matte black surface; however, 1/10 to 2/10 of a mil of thickness of the surface is removed and the geometry of the cutting edges are altered and the tapered point is blunted. The needle is unsuitable as a surgical needle.

EXAMPLE IV

Needles as described in conjunction with Example I are placed in an oxidizing bath. The solution used is an alkaline, oxidizing type, black oxidizing compound sold by Ethone, Inc., a subsidiary of ASARCO under the tradename Ebanon SS.52. The bath is maintained at a temperature of about 121° to 126° C. Some of the needles are pre-treated by electropolishing to activate the needle surface. In all instances, the untreated or pre-treated needles have a uniform black surface. In some instances, it is a shiny black surface. When these needles are tested for flaking, a blackened surface readily flakes and the needles are unsuitable for surgical use.

EXAMPLE V

Needles as described in conjunction with Example I are treated utilizing a molten salt bath of sodium dichromate. The molten bath is maintained at a temperature of 875° F. and the needles are placed in the bath for about 30 to 45 minutes. The resultant needles are tested for surface characteristics under a scanning electro microscope. The surface has been considerably roughened and penetration studies show considerable increases in the force to penetrate. The resulting needles are not suitable for surgical use. Though the process might be optimized to produce acceptable needles the hazards associated with this process render it unsuitable for desired commercial manufacture.

EXAMPLE VI

For comparative purposes, three needles were tested. Each needle was a straight needle, 22 mils in diameter made from 455 stainless steel. The first needle was treated in accordance with the method for the present invention. This needle was electropolished to activate the surface prior to the blackening treatment of the present invention. The second needle was buffed before being blackened according to the present method. The surface of this needle was buffed as described in Japanese Patent No. 45-19368. Both needles were tested for initial penetration force and for drag on the needle as it passes through penetration needle. An unblackened, electopolished needle was tested in the same manner. The following results were obtained:

| Needle | Initial Penetration Force (Grams) | Penetration Drag (Grams) |
| --- | --- | --- |
| Needle of Present Invention | 113 | 71 |
| Buffed Surface & Blackened Needle | 119 | 131 |
| Electropolished & Unblackened Needle | 117 | 35 |

Having now described the invention, it should be readily apparent that many variations and modifications may be made without departing from the spirit and scope of the present invention.

What is claimed is:

1. A chromium containing stainless steel, sterile surgical needle, said needle having a uniform black and non-reflective surface and said needle having penetration characteristics substantially the same as a sterile surgical needle having a shiny and polished surface.

* * * * *